United States Patent [19]

Meyer

[11] Patent Number: 5,288,149
[45] Date of Patent: Feb. 22, 1994

[54] GAS CALORIMETER AND WOBBE INDEX METER

[75] Inventor: Emilio Meyer, Assago-Milano, Italy

[73] Assignee: Panametrics, Inc., Waltham, Mass.

[21] Appl. No.: 850,044

[22] Filed: Mar. 12, 1992

[51] Int. Cl.$^5$ .............................................. G01N 25/22
[52] U.S. Cl. ........................................ 374/36; 374/37
[58] Field of Search ............................ 374/36, 37, 38; 73/863.01, 23.2, 23.31

[56] References Cited

U.S. PATENT DOCUMENTS

| | | |
|---|---|---|
| 2,944,418 | 7/1960 | Engelhardt . |
| 3,777,562 | 12/1973 | Clingman, Jr. . |
| 4,062,236 | 12/1977 | Clingman, Jr. . |
| 4,329,873 | 5/1982 | Maeda . |
| 4,329,874 | 5/1982 | Maeda . |
| 4,382,698 | 5/1983 | Szonntagh ............... 374/37 |
| 4,384,792 | 5/1983 | Sommers et al. ........... 374/36 |
| 4,386,858 | 6/1983 | Kude et al. ............... 374/37 |
| 4,511,262 | 4/1985 | Arcara .................. 374/36 X |
| 5,142,898 | 9/1992 | Kauschke et al. ......... 73/23.31 |

FOREIGN PATENT DOCUMENTS 0060681 11/1982 European Pat. Off. .
2074728A 4/1981 United Kingdom .

OTHER PUBLICATIONS

American Gas Association publication entitled New Approach to the Continuous Measurement of Calorific Values of Gaseous Fuels, (72-D-13), AGA Proceedings 1972, pp. D-64 through D-69.

*Primary Examiner*—Daniel M. Yasich
*Attorney, Agent, or Firm*—Lahive & Cockfield

[57] ABSTRACT

Apparatus for measuring the combustion characteristics of a gaseous fuel. Wobbe index and calorific value are measured with a fast response time by maintaining a stoichiometric mixture in a mixer supplied with the gaseous fuel at a constant pressure together with ambient air. The pressure of ambient air is controlled by measuring the residual oxygen from combustion of the mix and employing variations in that measured value to control the ambient air supplied to the mixer. The control signal for the ambient air is proportional to the Wobbe index. A separate measurement of the oxygen in the stoichiometric mix provides a signal proportional to the calorific fuel value.

11 Claims, 2 Drawing Sheets

GAS CALORIMETER AND WOBBE INDEX METER

BACKGROUND OF THE INVENTION

This invention relates in general to fuel gas analysis and more particularly to an apparatus and method for measuring the Wobbe index of fuel gas, together with the calorific value of the fuel gas.

There are a number of situations in which it is required to make a determination of the Wobbe index of a fuel gas as an indication of the efficiency of that mixture for combustion purposes. The well known Wobbe Index has been defined as the amount of heat released by a burner of constant orifice, McGraw-Hill Dictionary of Science, 1979. It is also desirable in many of these same situations to measure the calorific value of the fuel gas for determination of appropriate billing amounts. The calorific value has been defined as the quantity of heat liberated in a complete combustion of a unit weight or unit volume of fuel, Dictionary of Scientific and Technical Terms, McGraw Hill Book Company, 1974. The Wobbe index is inversely related to the square root of the density of the fuel gas mixture and directly proportional to the calorific value. The measurement of both the Wobbe index and the calorific value of fuel gases is done in a number of conventional systems employing conventional sensors. However, in addition to the obvious requirements of accuracy and reliability of such measurements, speed of response is important, but difficult to achieve.

It is therefore a primary object of the present invention to provide for measurement of Wobbe index and of calorific value of a fuel gas in a system which provides for rapid response time for measuring variations in the fuel. If these measured values are employed in a feedback system to control a process or if the calorific value is being used to provide a billing basis, then it is apparent that this rapid response time renders the entire system more efficient.

SUMMARY OF THE INVENTION

Broadly speaking in the present invention a fuel gas is provided through an orifice at a regulated pressure to a mixing chamber. The mixing chamber also receives ambient air from each of two capillaries. One capillary is provided at a constant pressure, while the air pressure in the other is controlled by a feedback loop. The constant pressure source provides the major portion (perhaps 90% of the total) of the air to the mixer, while the air from the second source is a controlled variable. The fuel input and air inputs to the mixer are adjusted initially with a known fuel gas to provide a stoichiometric mixture. This mixture is stoichiometrically balanced, that is, the quantity of reactants to be reacted in a chemical reaction are balanced such that there will be no residual reactants after that chemical reaction. This mixture is provided to an oxygen sensor of the high temperature zirconium oxide type. The sensor burns the stoichiometric mixture at high temperature and provides an output indication of the residual oxygen. This signal is converted in a controller/transducer to a pressure value controlling the variable air pressure supplied to one of the capillaries coupled to the mixer chamber. If the input fuel gas in the mixer chamber varies from the initial calibrated value so that it is no longer stoichiometric, then the change in residual oxygen sensed varies the air pressure applied to the mixer chamber, until the original stoichiometric balance is reachieved. This variation in air pressure or of the signal from the residual oxygen sensor is directly proportional to the Wobbe index.

A second oxygen sensor, in this instance not of a combustion type, but rather one which will measure the total amount of oxygen in the stoichiometric mix, is placed in parallel with the residual oxygen sensor to provide an output indication of the calorific value of the continuing flow of fuel gas.

DESCRIPTION OF PREFERRED EMBODIMENTS

Figure 1:
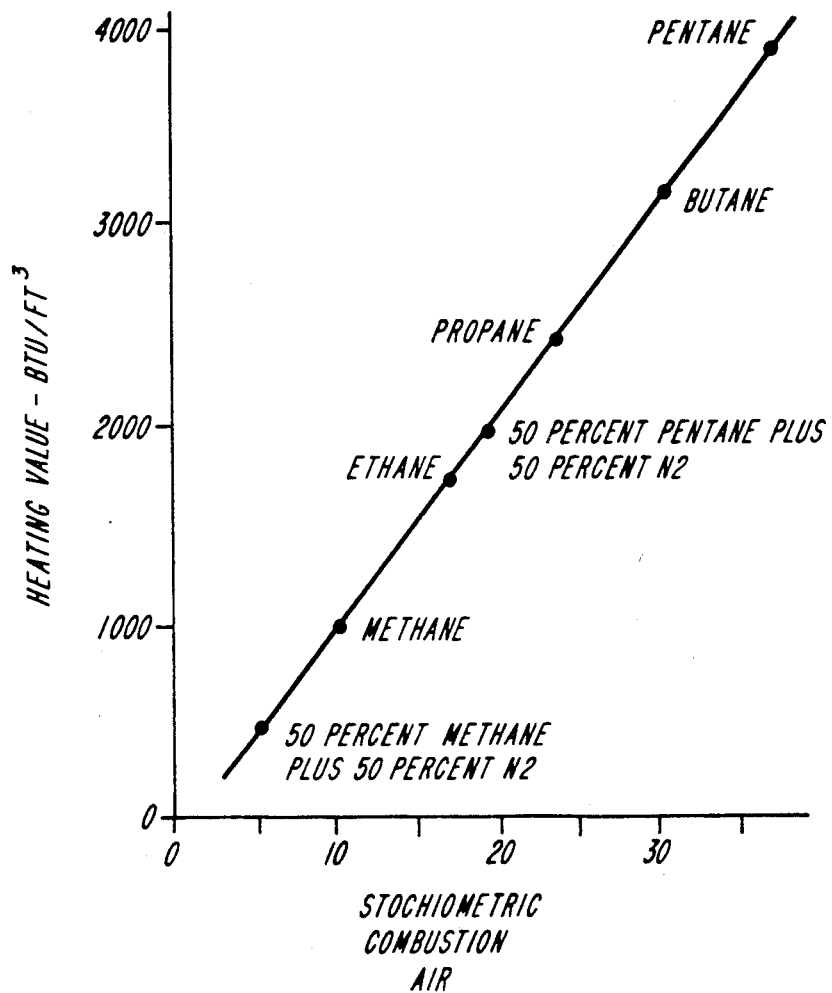
FIG. 1 is an illustration in graphic form of the relationship between calorific value and stoichiometric air in the fuel mixture.

FIG. 1 is an illustration of the relationship between stoichiometric combustion oxygen and the calorific value for some specific fuels. As shown this relationship is basically linear.

Figure 2:
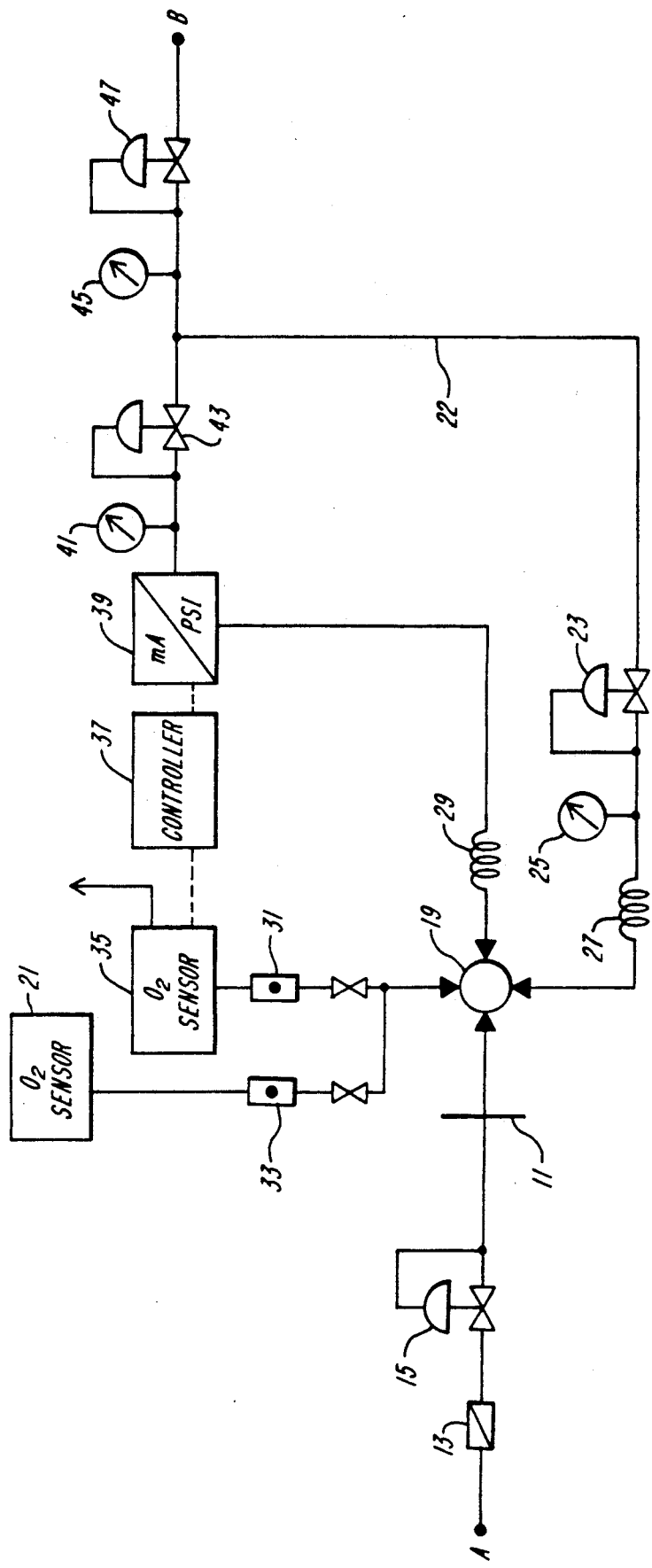
FIG. 2 is an illustration in generally diagrammatic form of a measurement apparatus for determining the Wobbe index and the calorific value of a fuel gas mixture supply on an ongoing basis.

FIG. 2 is a diagrammatic illustration of an apparatus for measuring the Wobbe index for a gaseous fuel sample and also for measuring the calorific value (the heating value) for that same gas sample. A sample of the fuel gas of interest is provided at inlet A and is coupled through a flashback arrestor 13 and a gas regulator 15 to orifice 11. A pressure gauge 17 in the line between the regulator and the orifice provides an indication of the input pressure to the orifice.

The output fuel gas from the orifice 11 is provided as one input to a mixing chamber 19. A second input to the mixing chamber 19 is supplied from air capillary 27. This capillary receives air at a substantially constant pressure through a line which originates at an air inlet B for ambient air, and is passed through air regulator 47 to a second stage air regulator 23. The pressure from air regulator 47 is indicated at gauge 45. The second stage regulator 23 may be adjusted to provide a flow of air through the capillary 27 to the mixer 19 so that this air supply, together with that supplied through capillary 29 provides a stoichiometric fuel/air mixture in the chamber 19. The output from the chamber 19 is supplied to a flowmeter 31 controlled by a valve to oxygen sensor 35. Oxygen sensor 35 is of the high temperature zirconium oxide type. The sensor burns the stoichiometric mix from the mixer 19 and senses the residual oxygen as a measure of any imbalance in either direction in the stoichiometric mix. Such sensors are characterized by a very fast response time (for example 90% of a step change is realized in less than one second) and can measure oxygen reliably and with high accuracy from proportions as small as a 0.10 ppm up to 100%. One commercially available oxygen sensor suitable for this purpose is a Series 350 Zirconia Oxygen Analyzer available from Panametrics, Inc. in Waltham, Mass., which unit provides an output electrical signal indicative of the oxygen excess in air/fuel mixtures.

The output signal from the oxygen sensor 35 is coupled to process controller 37, which in turn provides an output current signal, varying in response to variations in the sensed residual oxygen, to current/pressure converter 39. Such process controllers are well known in the art, suitable controllers are manufactured under the designation 300 series by Love Controller Corporation of Wheeling, Ill. The current to pressure converter 39, which is conventional in the art, receives a current signal from the process controller 37 and is supplied pressure from the pressure inlet B through the primary regulator 47 and secondary pressure regulator 43, the pressure from regulator 43 being indicated on gauge 41. The process controller 37 and the converter 39 together form a controller means for controlling the process of the first source of air in response to the residual oxygen measurement at sensor 35. The output pressure from converter 39 is then controlled to vary with variations in the input current from processor 37. This output pressure is provided through capillary 29 as an input to the mixer 19. Thus, the feedback loop formed by the elements from residual oxygen sensor 35 through the controller, converter and capillary, acts to maintain the mixture in the air fuel mixer 19 as a stoichiometric mixture by varying the air input in response to variations in the residual oxygen.

In the apparatus of FIG. 2 the flow through the gas orifice 11 can be expressed as $Q_g = K_g \sqrt{P/d}$ where $K_g$ is an appropriate proportionality constant, P is the pressure of the fuel gas as indicated by the gauge 17 and d is the density of fuel. The flow through capillary 27, is $$Q_a = \frac{KP}{\eta} = K_a P,$$

where $K_a$ is a suitable proportionality constant, P is the pressure sensed from regulator 23 as indicated by the gauge 25, and $\eta$ is the viscosity of the air.

As discussed above the air pressure supplied through capillary 29 is variable, being controlled through the feedback loop, but at a typical value for the relative flow of air from capillary 29 and that from capillary 27 the air from capillary 29, Qw, equals 0.1 $Q_a$ at a nominal 15 PSIG.

The Wobbe index is indicated either by the pressure value at the output of converter 39, or the current signal from process controller 37 at the input to converter 39.

The apparatus of FIG. 2 is shown with a second oxygen sensor 21 to which the stoichiometric mix is provided from mixer 19 through flow meter 38. The oxygen sensor 21 measures the total oxygen in the stoichiometric mixture. While there are many acceptable oxygen sensors to perform this function, a suitable one is commercially available from Panametrics, Inc. of Waltham, Mass. under the designation TM02D Oxygen Analyzer. The output signal from this second sensor 21 is a measure of the calorific value of the gaseous fuel.

A typical method of operation for this particular apparatus involve an initial calibration step in which fuel of a known composition is provided from fuel inlet A and the air supplied through capillaries 27 and 29 is adjusted so that a specific value of residual oxygen is detected in sensor 35, corresponding to a stoichiometric mix in chamber 19. The regulators 23 and 43 may be adjusted to provide for a desirable ratio between them for this initial setting.

Other specific apparatus may be employed to implement the method described herein for determining the Wobbe index and calorific value of a gaseous fuel. If, at the fuel input, the orifice 11 and regulator 15 are replaced with a suitable means for producing a constant flow, such as a volumetric pump, the air pressure from the converter 39 or the signal from the sensor/analyzer 35 represents directly the calorific value of the fuel, rather than the Wobbe index.

The invention having been described and specific embodiments having been set forth other implementations will be realized by those skilled in the art.

What is claimed is:

1. Apparatus for measuring the combustion characteristics, including the Wobbe Index, of a gaseous fuel comprising:
   a pressurized source of said gaseous fuel;
   an orifice connected to said pressurized source for passing said gaseous fuel;
   a pressure regulator positioned between said source and said orifice to control the pressure of said gaseous fuel supplied to said orifice;
   a mixer having first, second and third gas inputs and a gas output, said gaseous fuel from said orifice being supplied as a first input to said mixer;
   a first source of air supplied as a second input to said mixer;
   a second source of air supplied as a third input to said mixer at a predetermined, substantially constant pressure;
   an oxygen sensor for burning the output gas from said mixer, measuring residual oxygen and providing an output signal proportional to said measured residual oxygen;
   means for coupling said mixer output to said oxygen sensor;
   a controller means responsive to the output signal from said oxygen sensor for controlling the pressure of said first source of air in response thereto to maintain a stoichiometrically balanced air/fuel mixture in said mixer;
   the output signal from said oxygen sensor providing a measure of said Wobbe Index of said gaseous fuel.

2. Apparatus in accordance with claim 1 wherein said oxygen sensor provided an electric output signal and said controller means provides a pressurized air output signal having a pressure which varies in correspondence with variations in said electrical output signal.

3. Apparatus in accordance with claim 1 in which the combustion characteristics being measured include the calorific value, and including a second sensor for measuring the oxygen in said stoichiometrically balanced gaseous mixture supplied from the output of said mixer and providing an output signal indicative of the amount of oxygen in said mixture as indicate of the said calorific value of said gaseous fuel.

4. Apparatus in accordance with claim 1 wherein said oxygen sensor is of the zirconia oxide type.

5. Apparatus in accordance with claim 1 wherein the air supplied to said mixer from said first source is a fraction of the air provided to said mixer from said second source.

6. Apparatus in accordance with claim 5 wherein said second source of air includes a pressure regulator for adjusting the pressure supplied to said mixer.

7. Apparatus for measuring the combustion characteristics, including the calorific value, of a gaseous fuel comprising;
   a pressurized source of said gaseous fuel;
   a mixer having first, second and third gas inputs and a gas output;

means connected to said source for supplying said gaseous fuel at a constant volume of flow as a first input to said mixer;

a first source of air supplied as a second input to said mixer;

a second source of air supplied as a third input to said mixer at a predetermined, substantially constant pressure;

an oxygen sensor for burning the output gas from said mixer, measuring residual oxygen and providing an output signal proportional to said measured residual oxygen;

means for coupling said mixer output to said oxygen sensor;

a controller means responsive to the output signal from said oxygen sensor for controlling the pressure of said first source of air in response thereto to maintain a stoichiometrically balanced air/fuel mixture in said mixer;

the output signal from said oxygen sensor providing a measure of the said calorific value of said gaseous fuel.

8. A method for measuring the combustion characteristics, including the Wobbe Index, of a gaseous fuel supplied from a fuel sample inlet comprising the steps of;
   a) passing said gaseous fuel from said fuel sample inlet at a controlled pressure through an orifice;
   b) coupling the gaseous fuel from said orifice as a first input to a mixer;
   c) supplying air from a first source of air as a second input to said mixer to create a stoichiometrically balanced mix in said mixer;
   d) supplying air from a second source of air supplied as a third input to said mixer, at a predetermined substantially constant pressure;
   e) coupling said mixer output to an oxygen sensor for measuring residual oxygen by burning the output gas from said mixer, and providing an output signal proportional to the measured residual oxygen;
   f) controlling the pressure of said first source of air in response to said output signal to maintain a stoichiometrically balanced air/fuel mixture in said mixer and measuring said output signal from said oxygen sensor as a measure of the said Wobbe index of said gaseous fuel.

9. A method in accordance with claim 8 wherein said oxygen sensor provides an electrical output signal and wherein said electrical output is converted to a pressurized air signal having a pressure which varies in correspondence with variations in said electrical signal.

10. A method in accordance with claim 8 in which the combustion characteristics being measured include the calorific value and including the additional step of measuring the oxygen in said stoichiometrically balanced gaseous mixture supplied from the output of said mixer as an indication of the said calorific value of said gaseous fuel.

11. A method for measuring the combustion characteristics, including the calorific value, of a gaseous fuel supplied from a fuel sample inlet comprising the steps of;
   a) passing said gaseous fuel at a controlled flow volume from said fuel sample inlet as a first input to said mixer;
   b) supplying air from a first source of air as a second input to said mixer at a pressure to create a stoichiometrically balanced mix in said mixer;
   c) supplying air from a second source of air supplied as a third input to said mixer, at a predetermined substantially constant pressure;
   d) coupling said mixer output to an oxygen sensor for measuring residual oxygen by burning the output gas from said mixer, and providing an output signal proportional to the measured residual oxygen;
   e) controlling the pressure of said first source of air in response to said output signal to maintain a stoichiometrically balanced air/fuel mixture in said mixer and measuring said output signal from said oxygen sensor as a measure of the said calorific value of said gaseous fuel.

* * * * *